(12) United States Patent
Wozencroft et al.

(10) Patent No.: US 7,485,148 B2
(45) Date of Patent: Feb. 3, 2009

(54) PROSTHESIS

(75) Inventors: Robert Michael Wozencroft, Epsom (GB); John O'Hara, Birmingham (GB)

(73) Assignee: Finsbury (Development) Limited, Leatherhead, Surrey (GB)

( * ) Notice: Subject to any disclaimer, the term of this patent is extended or adjusted under 35 U.S.C. 154(b) by 292 days.

(21) Appl. No.: 11/110,646

(22) Filed: Apr. 20, 2005

(65) Prior Publication Data

US 2006/0052876 A1 Mar. 9, 2006

(30) Foreign Application Priority Data

Apr. 20, 2004 (GB) ................. 0408791.2

(51) Int. Cl.
*A61F 2/32* (2006.01)
(52) U.S. Cl. ............... 623/22.36; 623/22.21
(58) Field of Classification Search ... 623/22.21–22.46, 623/22.15, 23.43, 23.47
See application file for complete search history.

(56) References Cited

U.S. PATENT DOCUMENTS

| | | | |
|---|---|---|---|
| 3,780,918 A * | 12/1973 | Curtis | 224/165 |
| 4,961,748 A * | 10/1990 | Frey et al. | 623/22.21 |
| 5,931,870 A * | 8/1999 | Cuckler et al. | 623/22.21 |
| 6,620,200 B1 * | 9/2003 | Descamps et al. | 623/22.32 |
| 2001/0004694 A1 * | 6/2001 | Carchidi et al. | 606/73 |
| 2003/0171818 A1 | 9/2003 | Lewallen | |
| 2003/0214139 A1 * | 11/2003 | Nigam | 294/1.2 |

FOREIGN PATENT DOCUMENTS

| | | |
|---|---|---|
| EP | 0 605 368 A1 | 7/1994 |
| FR | 2 633 823 A1 | 1/1990 |
| FR | 2 798 841 A1 | 3/2001 |
| FR | 2 819 172 A1 | 7/2002 |
| FR | 2 827 503 A1 | 1/2003 |
| GB | 2347864 A * | 9/2000 |
| RU | 2 201 174 C2 | 3/2003 |
| WO | WO 95/15132 A1 | 6/1995 |
| WO | WO 99/22672 A2 | 5/1999 |
| WO | WO 01/70141 A1 | 9/2001 |
| WO | WO 03/013397 A2 | 2/2003 |

* cited by examiner

*Primary Examiner*—Bruce E Snow
*Assistant Examiner*—Megan Wolf
(74) *Attorney, Agent, or Firm*—Senniger Powers LLP

(57) ABSTRACT

An acetabular component prosthesis adapted for affixation in a recess in a pelvis, comprising:
  a cup shell having a generally convex outer surface adapted to be in contact with the bone in use, a generally concave inner surface and a rim;
  at least one pair of substantially adjacent flanges extending from the outer surface of the cup at a point proximal to the rim of the cup and angled at angle θ downwardly thereto;
  one flange of the pair being at an equal but opposite angle α to a plane extending across the apex of each of the flanges to the other of the pair; and
  at least one aperture in each of the pair of flanges through which in use fixation means may be passed to fix the cup into the recess in the pelvis.

19 Claims, 5 Drawing Sheets

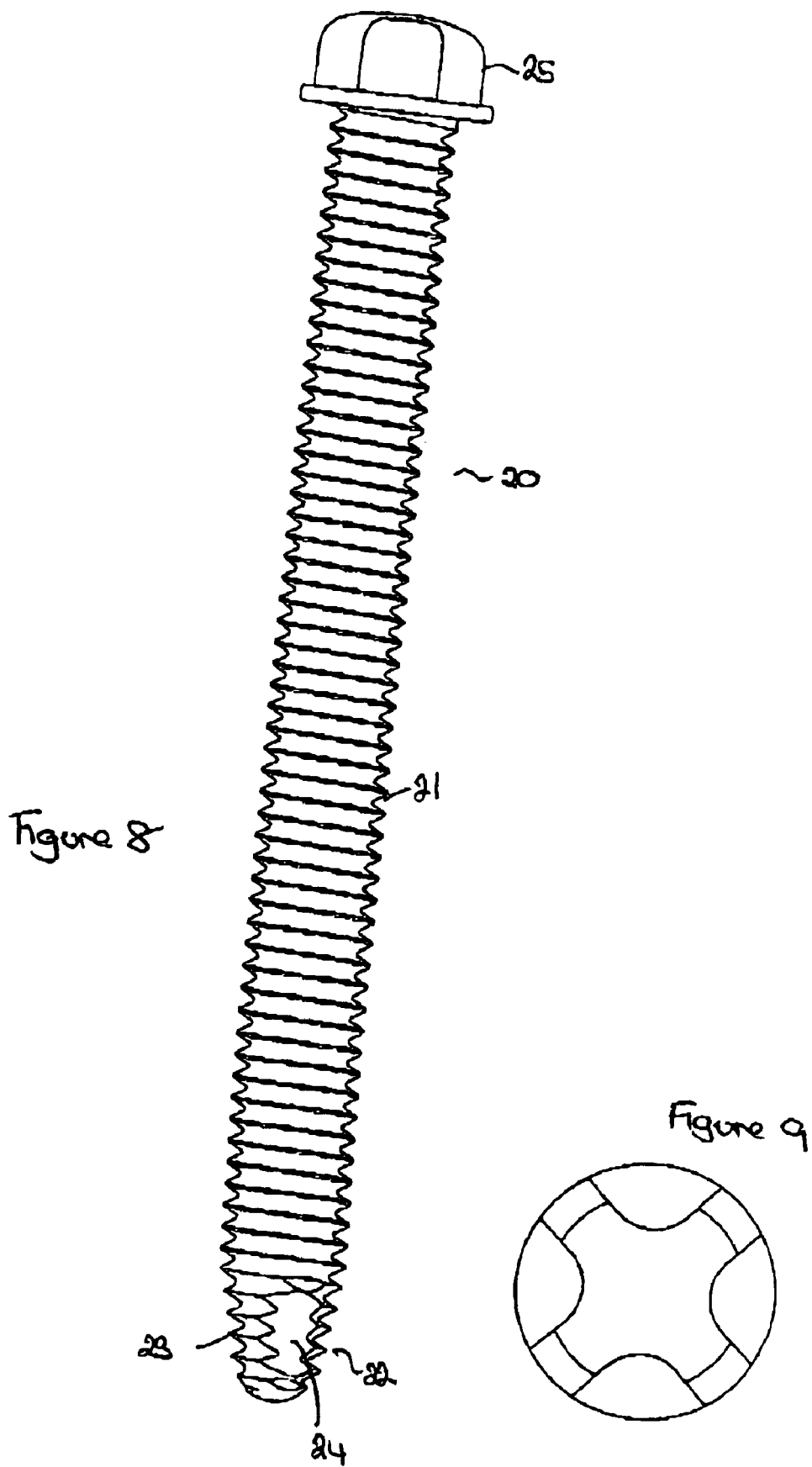

PROSTHESIS

FIELD OF THE INVENTION

The present invention relates to a prosthesis. More particularly, it relates to an acetabular component for a hip prosthesis.

BACKGROUND OF THE INVENTION

The efficient functioning of the hip joints is extremely important to the well being and mobility of the human body. Each hip joint is comprised by the upper portion of the upper leg bone (femur) which terminates in an offset bony neck surmounted by a ball-headed portion which rotates within a socket, known as the acetabulum, in the pelvis. Diseases such as rheumatoid- and osteo-arthritis can cause erosion of the cartilage lining of the acetabulum so that the ball of the femur and the hip bone rub together causing pain and further erosion. Bone erosion may cause the bones themselves to attempt to compensate for the erosion which may result in the bone being reshaped. This misshapen joint may cause pain and may eventually cease to function altogether.

Operations to replace the hip joint with an artificial implant are well-known and widely practiced. Generally, the hip prosthesis will be formed of two components, namely: an acetabular, or socket, component which lines the acetabulum (hereinafter an acetabular component); and a femoral, or stem, component (hereinafter the femoral component) which replaces the femoral head. During the surgical procedure for implanting the hip prosthesis the cartilage is removed from the acetabulum using a reamer such that it will fit the outer surface of the acetabular component of the hip prosthesis. The acetabular component of the prosthesis can then be inserted into place. In some arrangements, the acetabular component may simply be held in place by a tight fit with the bone. However, in other arrangements, additional fixing means such as screws or bone cement may be used. The use of the additional fixing means help to provide stability in the early stages after the prosthesis has been inserted. In some modern prosthesis, the acetabular component may be coated on its external surface with a bone growth promoting substance which will assist the bone to grow and thereby assist the holding of the acetabular component in place. The bone femoral head will be removed and the femur hollowed using reamers and rasps to accept the prosthesis. The femoral component will then be inserted into the femur.

In some cases, a femoral component of the kind described above may be replaced with components for use in femoral head resurfacing or for use in thrust plate technology.

Hip replacements do not have an infinite life. A major factor influencing the life expectancy of a prosthetic implant is wear of the articulating surface. The pressures acting on the implant contact surface can be of the order of 30 MPa/cm$^2$ during normal function. Over time wear debris is formed as the components of the hip replacement articulate against one another. These particles can cause osteolysis and adverse tissue reactions which will lead to loosening of the component and reduce implant life.

Currently the average life expectancy of a hip prosthesis is between 10 and 15 years. Where the implant has been placed in an elderly patient this period may be sufficient. However in a young patient, it is likely that one or more revision operations will have to be performed during the lifetime of the patient. One problem associated with these revision operations is that it is more difficult to get a tight fit between the replacement acetabular component and the pelvis due to further degradation of the bone.

In the case of the aforementioned revision operations, where there has been damage to the pelvis due to arthritis or in the case of patients suffering from dysplasia (shallow hip sockets), additional fixation means may be required to hold the acetabular component in place. In some arrangements, a hook feature may be included to hook around the edge of the pelvis adjacent to the obturator foramen.

Various proposals have been made with a view to providing improved acetabular component prosthesis which are particularly suitable for use with patients that are undergoing revision surgery, those whose pelvis is damaged or those who suffer from dysplasia.

RU2201174 describes an acetabular component which has a plurality of leaflets extending from the edge of the acetabular component which each include a hole through which fastening screws can be passed into the pelvic bone. The leaflets are bendable to conform to the shape of the pelvis. A hook is also included which is hammered into the bone tissue.

In EP0605368 a replacement acetabular component which is delimited by a circular flange is described. The flange is provided with a plurality of recesses for engaging therein radially extending elements which can be screwed to the pelvis. As this prosthesis has several separate elements, it can be difficult to fit.

WO95/15132 discloses an acetabular component which is held in place by screws inserted into the bone through the cup of the component. The cup is delimited by a flange which has holes therethrough which allows additional screws to be used. The acetabular component described in WO01/70141 is also held in place by means of screws placed through the side of the cup.

An alternative arrangement is described in WO99/22672. Here in addition to the cup of the acetabular component being held in place by means of screws which are passed through the wall of the cup, an extension through which screws may be placed is provided to enable the cup to be fitted in deficient acetabulae. The extension may be provided at selected angles depending on the acetabular defect which is to be treated. Alternative arrangements are described in WO03/013397 and US2003/0171818.

One problem associated with arrangements in which the cup is held in place by screws located through the cup is that interaction between the head of the femur may cause wear. It will be understood that the presence of screw holes in the cup disrupts the articulating surface which is disadvantageous particularly where the interface between the articulating components is metal/metal.

In FR2819172 a replacement acetabular component is described which includes a hook to engage the pelvic aperture and a rigid fixing lug extending from the component and angled thereto such that in use, when the component is placed in the orientation proscribed by the location of the hook, screws can be passed through holes in the lug to anchor the component in place. However, since the angling of the lug means that the acetabular component is orientation specific, separate components must be manufactured for the left and right side which increases the manufacturing costs.

An alternative arrangement is described in U.S. Pat. No. 6,620,200. The cup comprises a hemispherical part which is extended over substantially half the circumference of an equatorial edge of the hemispherical part and is defined by a plane inclined to the equatorial plane. The acetabular component is fitted with two extensions through which screws can be passed into the iliac. An obturator hook is located at a position diametrically opposite to a point situated at the center of the interval between the extensions.

While these acetabular components all go some way to providing an arrangement which can be readily attached to the pelvis, particularly in revision operations, in the treatment of dysplasia, or in an otherwise deficient pelvis, they suffer from various disadvantages and drawbacks. The modular systems can be expensive to manufacture and difficult to fit. Many of the systems only allow for short screws to be used due to the angle in which they are inserted into the bone and thus the support for the acetabular component may not be sufficient for prolonged use. Finally, the components may be orientation specific to only the left or right acetabulum thereby increasing the costs of manufacture. In some arrangements, the insertion of the screws may cause the acetabular component to be pulled out of alignment.

It is therefore desirable to provide an arrangement which overcomes the above-mentioned disadvantages. This can be achieved by the provision of an acetabular component which enables a fastening means to pass through a flange extending from and integral with the acetabular component in both a left-handed and right-handed manner such that the cup can be used in the left or right side of the pelvis.

SUMMARY OF THE INVENTION

Thus according to the present invention there is provided an acetabular component prosthesis adapted for affixation in a recess in a pelvis, comprising:
- a cup shell having a generally convex outer surface adapted to be in contact with the bone in use, a generally concave inner surface and a rim;
- at least one pair of substantially adjacent flanges extending from the outer surface of the cup shell at a point proximal to the rim of the cup and angled at angle θ downwardly thereto;
- one flange of the pair being at an equal but opposite angle α to a plane extending across the apex of each of the flanges to the other of the pair; and
- at least one aperture in each of the pair of flanges through which in use fixation means may be passed to fix the cup into the recess in the pelvis.

Since each flange of the pair of flanges is angled at an equal but opposite direction one of the flanges will be suitable to have fixation means passed therethrough when the cup is to be used in the left side of the body and the other is suitable when the cup is to be used in the right side of the body.

In a preferred arrangement of the present invention two pairs of flanges will be present. This enables two fixation means to be used thereby improving the strength of the attachment to the pelvis. It will be understood that corresponding flanges in each pair will preferably be positioned such that they are parallel.

In one arrangement the pair of flanges are contiguous. In the arrangement where there are two pairs of flanges, all of the flanges are contiguous such that a zig-zag arrangement of flanges is achieved.

As explained above, the pair of flanges are angled downwardly from the rim of the cup. This angle θ, which is defined with reference to the plane extending across the rim of the cup, may be selected to be any suitable angle which enables the fastening means to be inserted into the pelvis. Angles in the region of from about 0° to about 30° are suitable with angles of from 10° to about 25° being more preferred. In some arrangements, angles in the region of 20° offer various advantages. This arrangement will direct the screws into the available bone in such a manner that the longest possible fastening means may be used which will provide optimum support for the implant.

Each of the pair of flanges is angled at an angle α to a plane extending across the apex of each of the flanges. α may be of any suitable value which will enable the fastening means to be passed into the pelvis at an appropriate angle to hold the acetabular component in place. Angles in the region of about 10° to about 40° may be suitable. However, in order that the fastening means can be passed into the bone at the optimum angle such that they are loaded in compression, α is preferably in the region of about 20°. Having the fastening means loaded in compression reduces the risk of the fastening means failing with prolonged use.

The fastening means will preferably act as struts and thus in use will not pull the flange to the bone.

The apertures in the flanges are preferably threaded such that the fastening means may be screws. The screws are preferably arranged such that they are self-tapping into the bone.

The screws may be chosen to have deeper flutes at the tip end than have been used heretofore. In one arrangement, the thread may be tapered. One benefit of tapering the thread toward the tip is that the risk of cross-section as the screw is inserted into an aperture in the flange is reduced.

A further advantage of the use of the above described screw is that when the screw tip enters a pre-drilled hole in the bone, the edge of the hole will generally sit part way up the taper. Since the thread extends down the taper and is likewise tapered, the screw will immediately engage the bone and draw the cup inwardly. This is in direct contrast to the initial repulsion which is noted if a conventional screw is noted.

The head of the screw may be cross-headed. In one arrangement the cross is formed such that it is proud of the top of the screw. The arms of the cross may be shaped in any suitable configuration. Without wishing to be bound by any particular theory, it is believed that the surface provided by the cross-headed screw is more friendly to the surrounding tissue than the conventional hexagonal heads.

Thus according to a second aspect of the present invention there is providing fastening means comprising a screw having a threaded shaft and a tapered end which has a tapered screw thread.

The acetabular component of the above first aspect may additionally include a hook extending from the external surface of the cup which in use will hook round the edge of the obturator foramen to further assist holding the cup in position. Where the hook is present, the at least one pair of flanges will be located diametrically opposite the hook. The hook may be of any suitable configuration. Examples of hooks can be found in the prior art. Examples can be found in FR2710836, FR2819172, FR2660546, FR2334372, FR2595241, EP0605368, U.S. Pat. No. 6,620,200 and WO03/013397 which are incorporated herein by reference.

Each of the pair of flanges may include markings to enable the user to readily identify through which flange the fastening means should be placed depending on whether the cup is being used on the left or right side of the body. In one arrangement they will be marked "R" and "L" respectively although for use in non-English speaking countries, the appropriate designation for the translation of "right" and "left" may be used.

The cup may be of any suitable size. It may be hemispherical or shallower cups may be used. Larger cups may also be considered.

The acetabular component may be formed of any suitable material. It will preferably made from a biocompatible material such as titanium, a titanium alloy or cobalt-chrome. Alternatively it may be formed from a plastics material such as an epoxy resin material. The plastics material may be reinforced such as with carbon fibre.

Where required, the cup may be fitted with a liner. Liners may be made of any suitable material such as metal, ceramic or plastics material. The liner will generally be a snug fit in the bowl of the cup. Additional means may be provided to hold the liner in place. The insert may be retained in place by means of adhesive or by a press-fit or snap locking arrangement.

Some, or substantially all, of the external surface of the cup may be formed as a porous surface or in an alternative arrangement may be provided with a bone promotion layer, such as a layer of hydroxyapatite, so as to facilitate and promote bone ingrowth into the outer portion of the cup.

If required the cup of the present invention may in addition to the fastening means be cemented into position.

The cup of the present invention may additionally include other features known in the art. For example, elements may be included to allow further interaction with the bone, to allow interaction with tools used in insertion of the cup and/or to prevent rotation of the cup.

According to a third aspect of the present invention there is provided a kit of parts comprising an acetabular component prosthesis of the above first aspect and at least one fastening means. The fastening means is preferably the fastening means of any one the above second aspect.

BRIEF DESCRIPTION OF THE DRAWINGS

The present invention will now be described, by way of example by reference to the accompanying drawings in which:

FIG. 2 is an end elevation showing the flange end-on;

FIG. 8 illustrates a side view of a preferred fastening means; and

FIG. 9 is a view of the fastening means of FIG. 8 from above.

DESCRIPTION OF PREFERRED EMBODIMENTS

Figure 1:
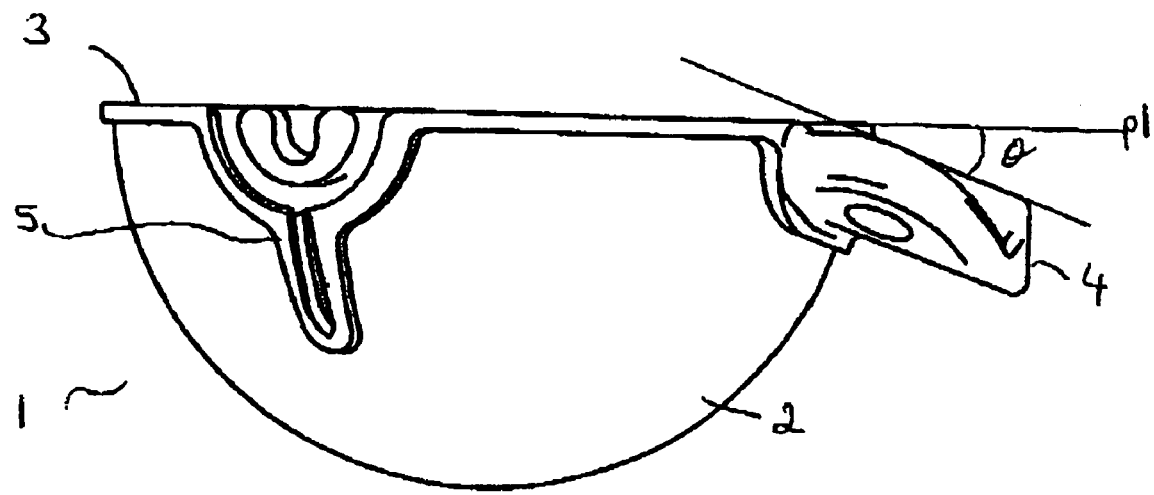
FIG. 1 is a side elevation of an acetabular component according to the present invention.
Figure 2:
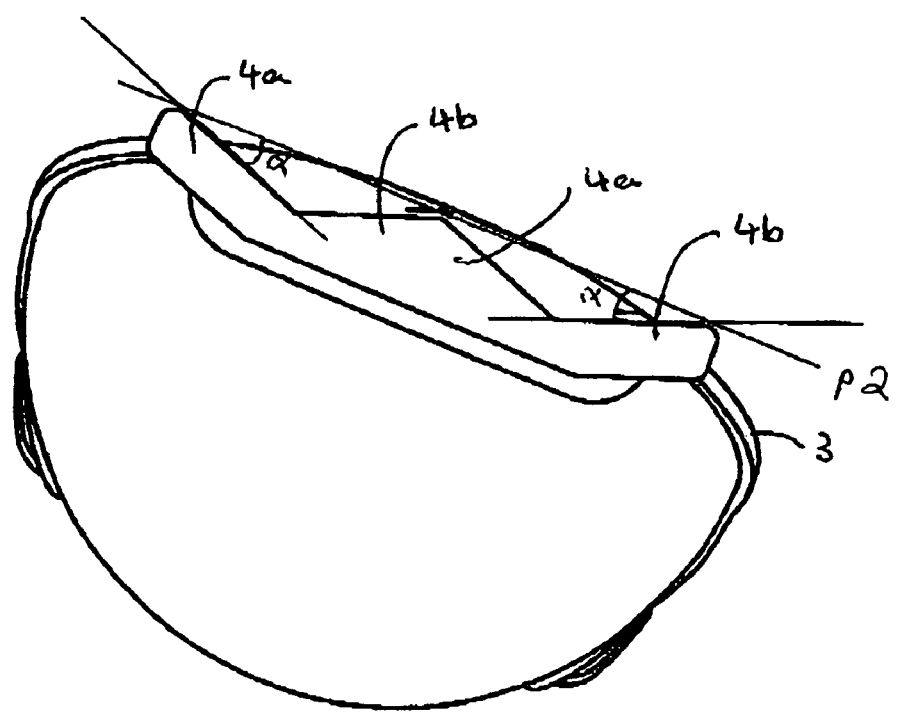

As illustrated in FIG. 1, the acetabular component of the present invention comprises a cup 1 which has a convex outer surface 2 and a rim 3. A pair of flanges 4 extends form the outer surface 2 at a point adjacent to the rim 3 at an angle θ to the plane p1 of the rim 3. In the illustrated embodiment θ is in the region of 20°. Lugs 5 may be present to prevent rotation and to facilitate the attachment of the cup to a gripping tool used during implantation. An example of a suitable tool can be found in GB2323036.

Where two pairs of flanges are used which are contiguous an arrangement of the type illustrated in FIG. 2 will be appropriate. Here each flange 4*a* and 4*b* is placed at an angle α to the plane p2 which passes through the apex of each flange. In the illustrated arrangement α is 20°. The two flanges making up each pair are at an opposite orientation and corresponding flanges from each pair are parallel. Thus the two flanges 4*a* are parallel as are the two flanges 4*b*. Flanges 4*a* and 4*b* together make up a zigzag arrangement.

Figure 3:
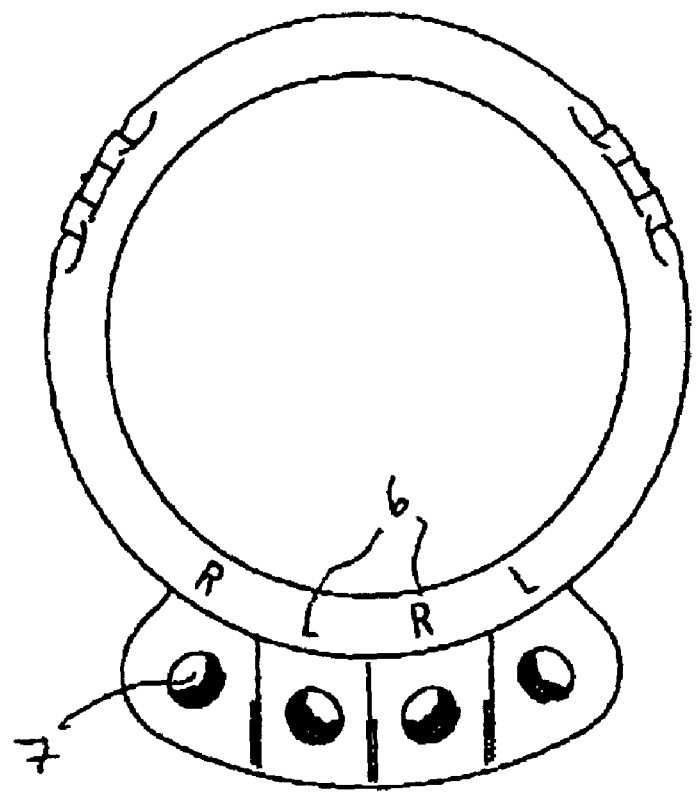
FIG. 3 is a view from above.

The flanges may be labeled to indicate whether they are for use when the cup is being applied to the left or right side of the pelvis. As illustrated in FIG. 3, the labeling 6 may be "L" and "R" for the left and right side respectively.

Figure 4:
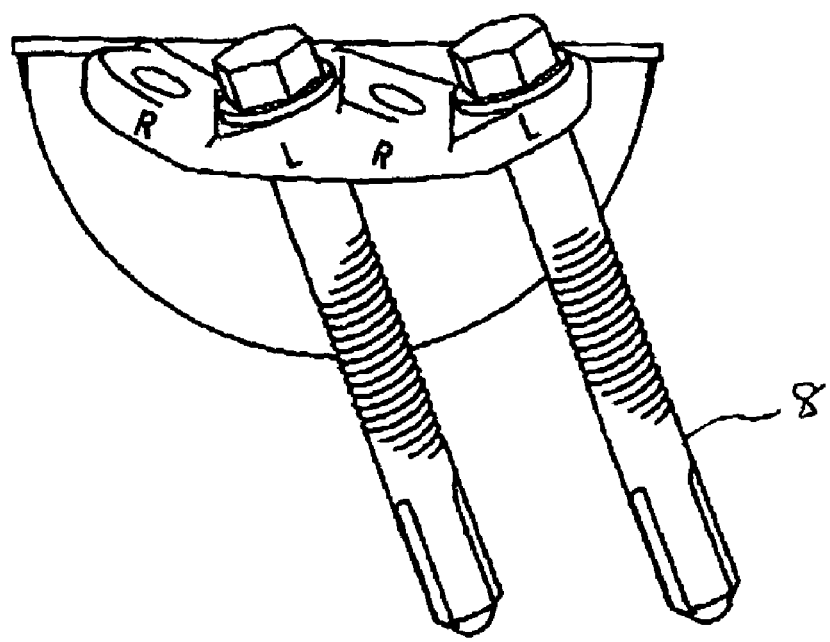
FIG. 4 is a view showing the cup with screws.

The apertures in the flanges 7 are threaded so that screws 8 may be used as the fastening means. As illustrated in FIG. 4, the use of corresponding parallel flanges for each side means that the screws 8 are held parallel at the optimum angle such that in use the screws are directed such that they enter the thickest part of the bone and act as struts.

Figure 5:
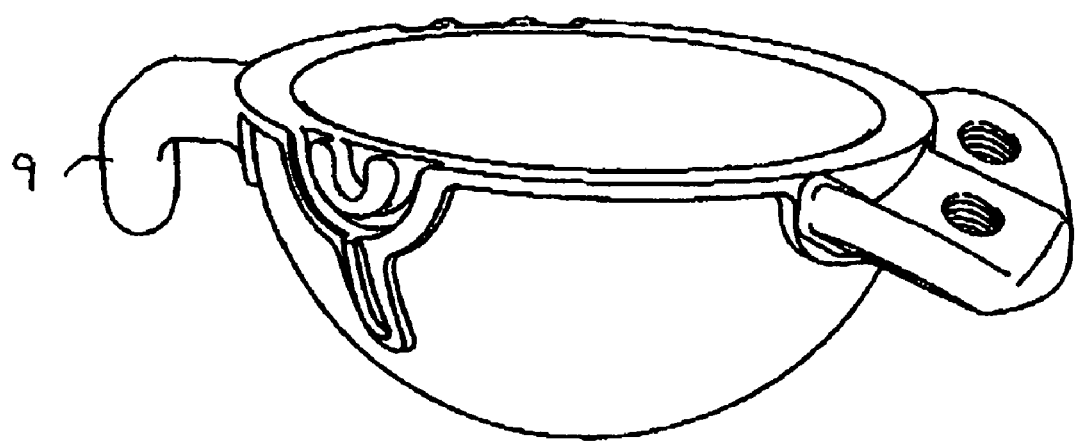
FIG. 5 is a view from one side and above showing the presence of the hook.
Figure 6:
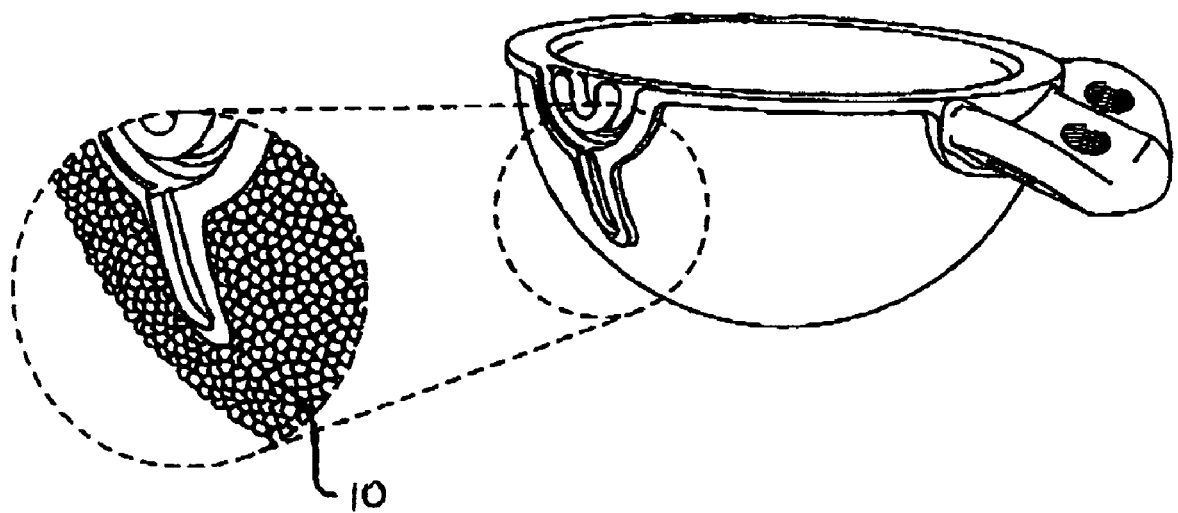
FIG. 6 is a side view of an embodiment without the hook with an exploded view illustrating the surface of the cup.

A hook 9 as shown in FIG. 5 can be included to hook around the pelvis at a point adjacent to the obturator foramen at a point diametrically opposite to the flanges. As illustrated in FIG. 6, the external surface of the cup may include surface structures 10 to promote bone growth.

Figure 7:
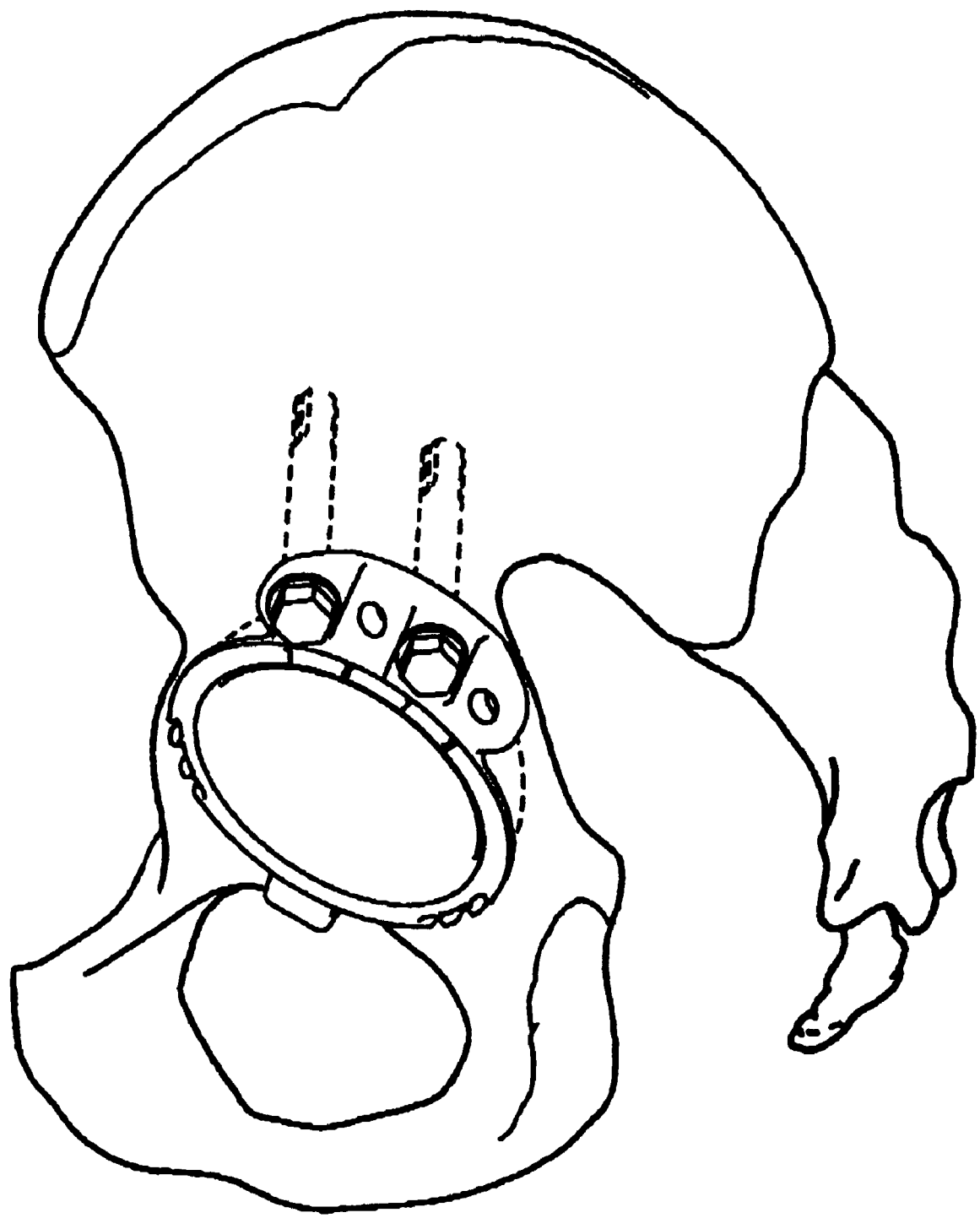
FIG. 7 illustrates the acetabular component of the present invention in use.

FIG. 7 illustrates the use of the cup of the present invention in the pelvis.

FIG. 8 shows the preferred fastening means of the present invention. The fastening means is a screw 20 having a threaded shaft 21 and a tapered end 22. The screw thread is also tapered 23. Flutes 24 are provided in the tapered end 22. These flutes are generally deeper than is conventionally used.

The head of the screw 25 may be of a cross configuration as illustrated in FIG. 9. The arms of the cross generally have rounded edges.

The acetabular component prosthesis of the present invention can be used with any arrangement of femoral component including those which could be described as a full femoral prosthesis component but also those used in resurfacing and in thrust plate technology. The component of the present invention may also be used with an natural femur head.

The invention claimed is:

1. An acetabular component prosthesis adapted for affixation in a recess in a pelvis, comprising:
    a cup shell having a generally convex outer surface adapted to be in contact with the bone in use, a generally concave inner surface opposite the outer surface, and a rim joining the outer and inner surfaces;
    at least two pair of adjacent generally planar flanges extending from the outer surface of the cup adjacent the rim of the cup and angled at an angle θ measured radially between a plane of the rim and the respective flange, one flange of each pair being at an angle α measured tangentially between a plane extending across an apex of the flanges and the respective flange, wherein the angle α of one flange of each pair is equal and opposite the angle α of the other flange of the respective pair and in a range from 10° to 40°; and
    an aperture in each flange adapted for receiving a fastener to fix the cup in the recess in the pelvis.

2. An acetabular component prosthesis according to claim 1 wherein two pairs of flanges are present.

3. An acetabular component prosthesis according to claim 2 wherein corresponding flanges in each pair are positioned such that they are parallel.

4. An acetabular component prosthesis according to claim 1 wherein each pair of flanges is contiguous.

5. An acetabular component prosthesis according to claim 2 wherein the two pairs of flanges are contiguous.

6. An acetabular component prosthesis according to claim 3 wherein each pair of flanges is contiguous.

7. An acetabular component prosthesis according to claim 1 wherein θ is from about 0° to about 30°.

8. An acetabular component prosthesis according to claim 1 wherein θ is from about 15° to about 25°.

9. An acetabular component prosthesis according to claim 8 wherein θ is 20°.

10. An acetabular component prosthesis according to claim 1 wherein α is 20°.

11. An acetabular component prosthesis according to claim 1 wherein the apertures in the flanges are threaded.

12. An acetabular component prosthesis according to claim 1 further comprising a hook extending from the outer surface of the cup.

13. An acetabular component prosthesis according to claim 12 wherein the hook is located diametrically opposite at least one pair of flanges.

14. An acetabular component prosthesis according to claim 13 wherein each of the pair of flanges includes markings to enable the user to readily identify through which flange a fastener should be inserted.

15. An acetabular component prosthesis according to claim 14 wherein the markings are "R" and "L".

16. A kit of parts comprising an acetabular component prosthesis of claim 1 and at least one fastener.

17. A kit according to claim 16 wherein the fastener comprises a screw having a threaded shaft and a tapered end having a tapered screw thread.

18. A kit according to claim 17 wherein flutes are provided in the tapered end.

19. A kit according to claim 17 wherein the head of the screw is of a cross configuration.

* * * * *